United States Patent [19]
Sanders

[11] Patent Number: 5,914,240
[45] Date of Patent: Jun. 22, 1999

[54] METHOD AND TEST KITS FOR DETECTION OF BACTERIOPHAGE

[75] Inventor: Michael F. Sanders, Basingstoke, United Kingdom

[73] Assignee: The Minister of Agriculture Fisheries & Food in Her Brittanic Majesty's Government of the United Kingdom and Northern Ireland, London, United Kingdom

[21] Appl. No.: 08/592,435

[22] PCT Filed: Jul. 29, 1994

[86] PCT No.: PCT/GB94/01649

§ 371 Date: Feb. 7, 1996

§ 102(e) Date: Feb. 7, 1996

[87] PCT Pub. No.: WO95/05483

PCT Pub. Date: Feb. 23, 1995

[30] Foreign Application Priority Data

Aug. 18, 1993 [GB] United Kingdom ............... 9317139

[51] Int. Cl.$^6$ .......................... G01N 33/554; A23C 9/12; C12M 1/32
[52] U.S. Cl. .............. 435/7.32; 435/5; 435/34; 435/36; 435/291; 435/292; 435/293; 426/34; 426/41; 426/43
[58] Field of Search ................ 435/5, 7.32, 34, 435/36, 291, 292, 293; 426/34, 41, 43

[56] References Cited

U.S. PATENT DOCUMENTS

| 4,104,126 | 8/1978 | Young | 195/103.5 |
| 4,218,534 | 8/1980 | LaBelle et al. | 435/5 |
| 4,861,709 | 8/1989 | Ulitzur et al. | 435/6 |
| 5,085,982 | 2/1992 | Keith | 435/5 |

OTHER PUBLICATIONS

Sigma Biochemicals, Organic Compounds Catalogue, "Adenosine 5'–Triphosphate (ATP) Bioluminescent Assay Kit", p. 51, 1992.

*Primary Examiner*—James C. Housel
*Assistant Examiner*—Rodney P Swartz
*Attorney, Agent, or Firm*—Nixon & Vanderhye P.C.

[57] ABSTRACT

A method for detection, identification and/or quantification of bacteriophage of bacterial host specificity for bacterial genus, species or serotype, based upon the occurrence of release of cell contents, particularly nucleotides e.g. ATP, on lysis of bacterial cell walls on incubation with bacterial host cells. When new phage particles are released at the end of the phage replication cycle nucleotide levels are measured and compared with controls. The method provides for the detection of specific phages which is faster and more sensitive than known techniques. The method is only limited by the availability of host bacteria/target phage pairings.

12 Claims, No Drawings

METHOD AND TEST KITS FOR DETECTION OF BACTERIOPHAGE

The present invention relates to a method of detection, identification and/or quantification of bacteriophage (phage or phages), and to test kits for use in carrying out that method. Particularly the method enables detection of bacteriophages specific to particular bacterial genus, species or serotype, whether in isolated form or as contaminants in environmental or forensic samples, or in foodstuffs.

Although often undesirable, bacteria also have many industrial applications. Increasingly important is the role of bacteria in the area of genetic engineering and particularly in the large scale production of protein products as genetically engineered bacteria. More traditionally they have been used in production of natural products in fermentation, notably in production of cheese and milk fermentation products. The rapid fermentation of lactose to lactic acid is the principal reaction in the manufacture of such milk derived products and is initiated by the addition of starter cultures of species of lactic acid bacteria to the milk substrate. On occasion, for various reasons, these starter cultures fail and normal acid development fails to begin or is not maintained.

One of the most important reasons for starter culture failure is the presence in the milk of bacteriophage, often originating from the dairy environment. These are specific viral agents that attack and kill bacteria, in this case those of the starter culture. The bacteriophage reproduce parasitically in their bacterial hosts, resulting in a progeny of new phage particles which are liberated into the environment upon lysis of the bacterial cells. A bacteriophage infection in a dairy plant results in a serious decrease and, in some cases, a total failure in the production of lactic acid by the starter cultures. For many years the problem of phage has been the most serious one confronting the cheesemaker because of the economic losses it entails. These include the time lost in manufacture, loss of the raw material and of substandard product (see Klaenhammer (1984) Adv. Appl. Microbiol. 46, 313–25 and Heap & Lawrence (1988) Developments in Food Microbiology, Elsevier). Conventional techniques used in the dairy industry for bacteriophage detection are based upon traditional microbiological technology, and are both labour intensive and time consuming. These include observation of bacterial plaques, ie. clear areas in a background of bacteria, produced on lawns of starter culture bacteria in petri dishes and measuring the rate of lactic acid production in cultures, both inoculated with environmental samples. It is clear that the development of a rapid yet simple bacteriophage detection technique would be of immense benefit to the industry.

The present inventor has now provided such a technique, which in its preferred form uses bioluminescent techniques to provide a light signal indicative of the presence and amount of a specific bacteriophage or bacteriophage type in a sample under investigation, giving a positive result within about 4 to 5 hours, as opposed to 24 hours or more for existing methods.

The method of the invention is based upon the release of cellular components from bacteria infected with bacteriophage, particularly when the bacteriophage undergoes lytic cycle replication. In this cycle the bacteriophage take over the metabolism of the cell and replicate themselves, whereby at the end of the cycle the bacterial cell walls rupture to release progeny and substantially the entire bacterial cell contents. By measuring one or more particular components found associated with the bacterial cell that are made accessible to reagents in an incubation medium by the phage it is possible to measure infection, eg. via lysis, and using calibration curves or other statistical techniques, it is thus possible to estimate the amount of phage in the original sample. By exposing the sample to a bacteria that is a specific target of the phage which is the subject of a test, and providing incubation conditions that would allow infection of that bacteria by the specific phage, it is possible to determine presence and amount of specific phage, even in the presence of those that do not cause infection, by assaying for particular cellular components made accessible as described above.

The present invention thus provides a method for the detection, identification and/or quantification of target bacteriophage of predetermined bacterial host specificity in a material under investigation comprising incubating a sample derived from the material with bacteria of that host type, preferably in a liquid culture, under conditions such that they are caused to release cellular components if infected with the target phage, measuring the amount of one or more particular components released from the bacteria by any bacteriophage present in the sample during the incubation, and relating this to the presence, identity and/or amount of target bacteriophage. Preferably the particular component or components comprise nucleotides.

It is theoretically possible to measure any of the nucleotides that are released by the cell lysis caused by the release of new phage particles, for example NAD, NADP. NADH, NADPH, ATP or ADP, cAMP or cGMP, with sensitivity provided by use of one or more of the many enzyme based assay systems, eg. 'cascade' systems, that are available in the art. For example, GB 2213261 discloses a method which may be used for assaying reduced pyridine nucleotides, eg NADH or NADPH, based upon a salicylate monooxygenase system, while other enzyme systems such as the alkaline phosphatase (EC 3.1.3.1)/NAD/NADP system as disclosed in GB 2240845. Suitable assay systems for ADP, cAMP, cGMP etc will occur to those skilled in the art.

However, particularly preferred is the measurement of adenosine triphosphate (ATP), that being readily measurable by assay with a variety of enzyme/enzyme substrate combinations by virtue of its being a cofactor in numerous substrate conversions, and being released in relatively large quantities as compared with other bacterial nucleotides. For the rapid and efficient determination of levels of released ATP in the present application it is especially preferred to utilise enzymes which result in the production of luminescence, most conveniently the enzyme luciferase. ATP release is quantifiable with commercially available reagents using the process of bioluminescence wherein it is used to drive the reaction in which luciferase catalyses the oxidation of luciferin resulting in the emission of light. The quantum efficiency of this reaction is extremely high and the amount of light produced gives a measure of the amount of AWP originally present in the sample before the assay reaction depleted it.

For identification or quantification of specific phage occuring in material in relatively high concentrations, eg. in cultures of isolated phage, it is possible merely to incubate the specific host bacteria with a sample of the material in the presence of, or with subsequent addition of, the component assay reagents and thus to measure the amount of component released by performing the assay.

Where lytic phages are being targeted, at the end of the replication cycle the specific host bacteria infected by the target bacteriophage burst (times range from eg. 20–60 minutes depending on species), cellular component, eg nucleotide, is released and detected by the assay. Control samples either containing no phage or phage without bacteria show no increase in levels above background levels.

For identification, detection and/or quantification of specific phage at lower concentrations, for example as contaminants in or on water or foodstuff materials, it is necessary to first perform an enrichment of the sample under test, eg. for a few hours, to allow the target phage to multiply to a level where released components. eg. nucleotides, will be detectable above background levels. This enrichment is preferably carried out by inoculating using a culture, preferably a log phase culture, of further host bacteria of type capable of being parasitised by the target bacteriophage, preferably specifically.

After the incubations with the host bacteria to increase phage count a sample of cell free phage enriched medium is mixed with a culture of the starter organisms, preferably in log phase, and incubated for a set temperature for a set time selected to cause release of cell component, these being dependent upon the characteristics of the phage/bacteria combination being used and the component, eg. nucleotide, whose release is to be measured using an appropriate assay, eg. enzyme/substrate system.

The sample to be analysed should preferably be filtered to remove any bacteria before being added to the enrichment or component release step, thus avoiding possible interfering release due to the action of non-target bacteriophage on contaminating bacteria. For the purpose of taking samples from an environment under investigation, conventional techniques may be used such as swabbing, eg. of surfaces, or sampling aliquots of liquids.

Dependent upon the biology of the phage/host pair selected, the method has the potential for great specificity and still further sensitivity and rapidity. Utilising the aforesaid ATP assay method the inventor has readily developed systems capable of the detection of phage specific to *Staphylococcus aureus, Listeria monocytogenes*, Salmonella, *E. coli* and pseudomonads. Those skilled in the art will appreciate that there is no limit to the application of the present method other than the availability of necessary specific phage/bacteria pairings. For the preferred luminescence assay method whereby ATP release is measured the test sample, whether enriched or not for phage, is conveniently mixed with the bacterial culture, preferably as log phase, in a luminometer tube and incubated for a suitable time. This will commonly be from 30 to 60 minutes depending on the phage/bacteria system. After or over this period, preferably after, the released ATP is measured using a light producing assay, eg. the luciferin/luciferase reaction system, to produce an amount of light which is detected in a luminometer and related to the amount of ATP.

In all cases controls may advantageously be carried out for comparison of background component levels, eg. nucleotide levels, eg. in samples of log phase culture medium without the bacteria and/or incubated with bacteria and a known amount of the phage, thereby enabling production of calibration curves. Such controls may include challenge with other hosts of different specificity for determining more completely the characteristics or various types of phage present in the sample. Similarly several bacterial types may be used in one incubation where the method is being used to screen for a number of types of phage for which no one common bacteria is specific enough.

The range of bacteria available and the bacteriophage for which they are specific will be realised to be vast by those skilled in the art. For example a list of phage types available from the American Type Culture Collection (ATCC) is published by them as the 'Catalogue of Bacteria & Bacteriophages'. Other such depositories also publish equivalent data in their catalogues and this may be used to identify possible phage 'reagents' for the present method. Bacteria may be used, inter alia, in aqueous suspension or in freeze dried form eg. on microtitre plate wells. In this manner plate luminometry can be used. The method of the invention is particularly intended for use to detect and quantify lytic phages, ie. those that lead to lysis of the test bacteria, but any phage that causes release of cellular components by its actions may be detected.

The present invention also provides test kits for carrying out the method of the present invention and these are characterised in so far as they comprise a bacteria selected for the ability to be infected specifically by target bacteriophage, ie. a type or types for which detection, identification and/or quantification is desired, in combination with some or all of the reagents which are specifically associated with the aforesaid method of the invention.

Thus preferably test kits of the present invention comprise (a) a bacteria selected for its ability to be specifically infected by target bacteriophage and caused to release cellular components thereby, and at least one of (b) the reagents necessary for carrying out assay for cellular component released by action of the bacteriophage on the bacteria and (c) a bacteria for supporting growth of target bacteriophage.

Thus preferred test kits of the invention are those wherein the reagents necessary for carrying out assay are for assay of the amount of a nucleotide released by the bacteria, preferably reagents comprising luciferin and luciferase. Test kits optimised for performance of high sensitivity assay of bacteriophage will include bacteria of component (c) above, which may be the same as those of component (a), but may also be less specifically parasitized bacteria which nevertheless are capable of supporting more rapid replication of phage or producing a higher quantity of phage.

The method and kits of the present invention will now be exemplified by way of illustration only by reference to the following non-limiting examples. The vast variety of options available will be readily determinable by those skilled in the art on consideration of the general method described above and particularised below, and the available types of bacteria/phage pairings and eg. nucleotide assays.

EXAMPLE 1

Kit for Use in the Detection of Bacteriphages Specific for Bacterial Starter Cultures in the Dairy Environment and in Dairy Products.

A kit for use in the method of the invention conveniently comprises the items marked with an asterisk below and optionally supplemented with any of the other equipment and reagents set out below as required for the method of the Example.

Equipment required: Sterile cotton swabs; 0.8 $\mu$m pore-size syringe filters; 0.22 $\mu$m pore-size syringe filters; sterile 5 ml syringes; sterile universal bottles or bijou bottles; centrifuge tubes; luminometer (model LB953 Autolumat; Berthold Instruments UK Ltd, St Albans, Hertfordshire); polystyrene luminometer tubes (Sarstedt. Beaumont Leys, Leicester).

Reagents required: Sterile peptone/saline (1 g per liter/8.5 g per liter distilled water respectively); M17 broth (Unipath Limited, Basingstoke), *Adenosine-5'-triphosphate assay mix containing luciferin/luciferase and dilution buffer (Sigma Chemical Company Limited, Poole, Dorset); sterile 10% lactic acid; *stock culture of starter culture bacteria (See Bulletin of the IDF 263/1991 Chapter 2).

EXAMPLE 2

Method for Detection of Bateriophages Specific for Bacterial Starter Cultures (A) in the Dairy Environment and (B) in Dairy Products, A: Dairy equipment method:

Sampling: A sterile cotton swab dampened in sterile distilled water was used to swab an area of equipment (0.5 square meters) and then agitated in 5 ml sterile peptone/saline. The peptone/saline was then filtered through a 0.8 µm pore-size syringe filter into a sterile container, then filtered again through a 0.22 µm pore-size syringe filter into a second such container. If bacteriophage liter was anticipated as being low a phage enrichment step was carried out.

Enrichment: 8 ml of fresh M17 broth was inoculated with 1 ml of log-phase culture of the starter organisms, 1 ml of the bacteriophage filtrate was added and the mix incubated at a suitable temperature for 4 hours (20–22° C. for mesophilic starter cultures and 42° C. for thermophilic starter cultures). This enriched culture was transferred to a centrifuge tube and spun to remove bacteria (5000 g for 20 minutes), before the supernatant was filtered through a 0.22 µm pore-size syringe filter into a sterile vessel.

Assay: 50 µl of M17 broth, held at between 22° C. or 42° C. depending on host starter culture used as set out above, was added to all 80 polystyrene luminometer tubes in the luminometer, prewarmed to the same temperature. 50 µl of a log-phase starter culture was placed into each alternate tube to act as negative control, and 0.5 ml of 'phage' filtrate from the enrichment or the sampling step was added to 4.5 ml of the remaining culture and 50 µl of this placed in each of the remaining luminometer tubes. Light measurement was commenced with 100 µl luciferin/luciferase reagent injected into each tube and the light output measured over periods of 60 seconds. Peak light measurements (counts per second) were then plotted against time for both sample and negative control tubes.

Result: An approximate 5 fold increase in free ATP levels of the test samples against the negative controls were shown to indicate presence of starter-specific phages in the test sample.

B: Dairy product method:

Sampling: Liquids required no particular pretreatment; powders advantageously were suspended in an appropriate volume (eg. 1:10 dilution) of sterile water; solids such as cheese were mixed with nine times their weight of peptone/saline then homogenised. The pH of all samples was adjusted aseptically to 4.5–4.7 to precipitate casein. 0.3 ml sterile 10% lactic acid was added to 10 ml milk or whey; pH electrode use was avoided unless autoclaved due to risk of contamination. The samples were centrifuged at 5000 g for 20 minutes and the supernatant filtered through a 0.22 µm pore-size syringe filter into a sterile container to remove large particles and bacteria. As in (A) above, the bacteriophage titre in this sterile filtrate was increased by an enrichment step if suspected to be low. Enrichment and light measurement steps were performed as described in Method A above.

I claim:

1. A method for the detection, identification and/or quantification of target bacteriophage of predetermined bacterial host specificity in a sample under investigation, said method comprising the successive steps of:

(a) enriching the bacteriophage present in the sample by incubating the sample with a culture of host bacteria capable of being parasitised by the target bacteriophage wherein it is allowed to multiply;

(b) incubating the enriched sample with bacteria of that host type in the presence of or subsequently adding an enzyme assay reagent under conditions selected such that the bacteria are caused to release cellular components if infected with the target bacteriophage;

(c) measuring the amount of one or more particular components released from the bacteria by any bacteriophage present in the sample during the incubation; and (d) relating the value measured in step (c) to the presence, identity and/or amount of target bacteriophage.

2. A method as claimed in claim 1 wherein the particular cellular component or components measured comprise one or more nucleotides.

3. A method as claimed in claim 2 wherein the component or components measured are one or more of NAD, NADP, NADH, NADPH, ATP or ADP, cAMP or cGMP.

4. A method as claimed in claim 2 wherein the nucleotide is measured using an enzyme based assay system.

5. A method as claimed in claim 4 wherein the assay system is an enzyme cascade assay.

6. A method as claimed in claim 1 wherein the component is ATP and the assay is one that uses an enzymic reaction resulting in luminescence.

7. A method as claimed in claim 6 wherein the assay system is the luciferin/luciferase system.

8. A method as claimed in claim 1 wherein the luciferin/luciferase reaction reagents are used and the amount of light given off is measured during and/or at the end of the incubation.

9. The method as claimed in claim 1 wherein the enrichment incubation of step (a) is carried out for 1 to 4 hours.

10. The method as claimed in claim 1 wherein the enrichment step of step (a) is carried out by adding the sample to a log phase culture of host bacteria.

11. The method as claimed in claim 1 wherein the enrichment and component release incubations of steps (a) and (b) are carried out using a number of different specificity host bacteria types whereby the release of component is indicative of a number of bacteriophage types.

12. A method as claimed in claim 1 wherein the sample to be analyzed is filtered to remove any bacteria before being added to the enrichment or component release steps.

* * * * *